United States Patent [19]

Elliott et al.

[11] 4,041,931
[45] Aug. 16, 1977

[54] RADIOPAQUE ANASTOMOSIS MARKER

[76] Inventors: Donald P. Elliott, 70 Eudora, Denver, Colo. 80220; William L. Halseth, No. 3 Ponderosa Circle, Parker, Colo. 80134

[21] Appl. No.: 687,034

[22] Filed: May 17, 1976

[51] Int. Cl.² ............................................. A61B 19/00
[52] U.S. Cl. ....................................... 128/1 R; 3/1.4; 24/27; 24/256; 116/124 R; 128/334 R
[58] Field of Search .................. 128/1 R, 303, 334 R, 128/334 C, 346; 3/1.4; 116/114 R, 124 R; 40/23 R, 316; 24/27, 257, 256, 261 AC; 85/8.6, 8.8; 174/94

[56] References Cited

U.S. PATENT DOCUMENTS

| 873,762 | 12/1907 | Lyons | 24/257 R |
| 911,583 | 2/1909 | Focht | 24/256 |
| 3,194,239 | 7/1965 | Sullivan | 128/335.5 |
| 3,875,928 | 4/1975 | Angelchik | 128/1 R |

FOREIGN PATENT DOCUMENTS

| 23,081 | 4/1907 | United Kingdom | 24/257 R |

OTHER PUBLICATIONS

Cheanvechai et al., Annals of Thorac. Surg., vol. 15, No. 2, Feb. 1973, pp. 210-212.

*Primary Examiner*—Dalton L. Truluck
*Attorney, Agent, or Firm*—Edwin L. Spangler, Jr.

[57] ABSTRACT

This invention relates to split ring markers fabricated in whole or in part from a radiopaque material, usually metal, having the terminal ends thereof and a medial portion formed to define eyelets by means of which said marker can be sutured to the tissue at the site of an anastomosis to provide a visual indication of its location when examined fluoroscopically.

4 Claims, 4 Drawing Figures

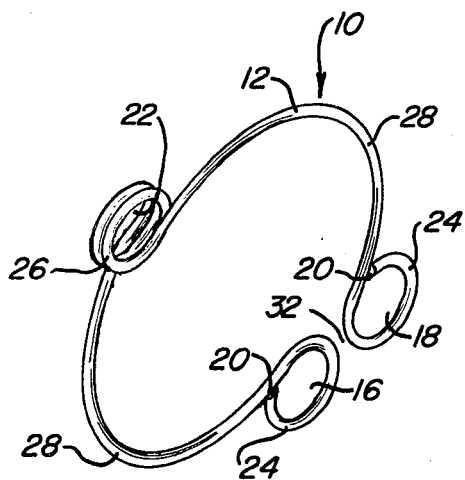
Fig_1
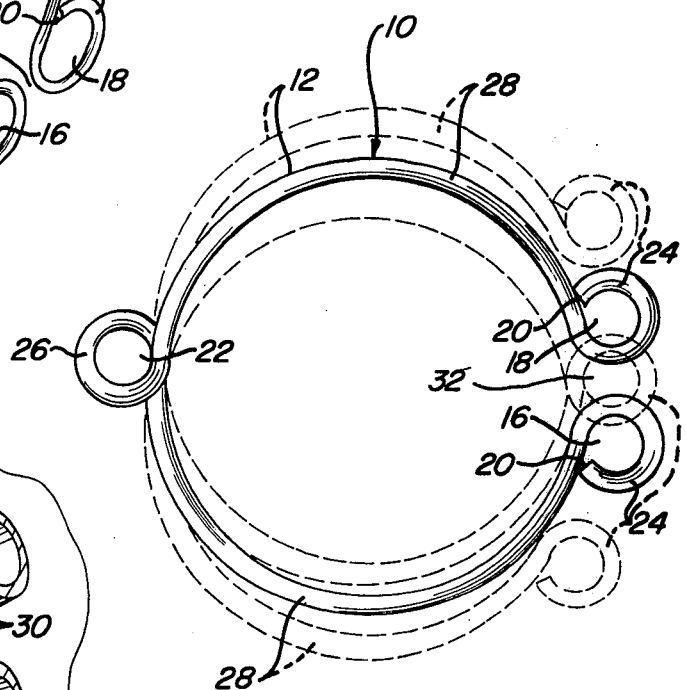
Fig_2
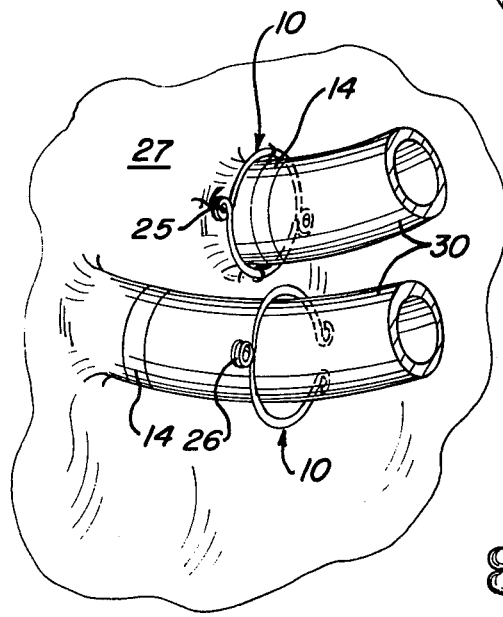
Fig_4
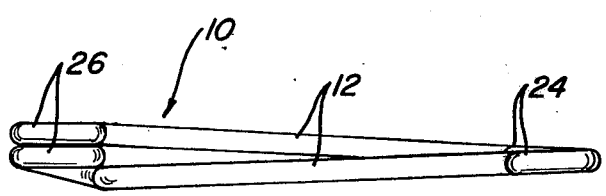
Fig_3

RADIOPAQUE ANASTOMOSIS MARKER

In surgical as distinguished from pathological anastomoses, occasions frequently arise where the site of the anastomosis must be examined fluroscopically. For instance, in coronary artery by-pass surgery, a section of one of the saphena veins from the patient's leg is removed surgically and reconnected to the aorta so as to bridge the blocked or otherwise damaged portion thereof. While the cardiovascular surgeon that performed the coronray artery by-pass will check to see that is is functioning properly before the chest cavity is reclosed, he or she may also wish or need to restudy the anastomoses afterward. Also, the cardiologist in subsequent cardiac catheterizations must be able to locate the exact site of each saphenous vein-aortic anatomosis.

The use of some sort of radiopaque metal tag to mark the site of each anastomosis is known in the prior art and constitutes a common practice, especially among cardiovascular and thoracic surgeons who are called upon to perform such procedures quite frequently and in more critical areas than is the case with most of the other surgical specialties. These tags have been in the form of a clip or washer designed to be fastened alongside the graft rather than in encircling relation thereto. As such, they have proven unsatisfactory in that they fail to delineate the exact location of the anastomosis with the degree of precision demanded by the surgeon or cardiologist in subsequent radiological examination.

It would seem that while performing coronary artery by-pass surgery, it would be a simple matter to slip a continuous ring over a free end of the saphenous vein before it is grafted onto the aorta to complete the anastomosis; however, such is not the case due to the urgency in completing the procedure and other factors. On the other hand, once the by-pass is complete, a half hour or so is available while the things are being checked out and before the chest cavity is reclosed during which such markers can be implanted.

A simple split ring is unsatisfactory in that it has sharp ends which can puncture or otherwise damage the adjacent tissue and create more problems than it solves. In addition, such rings become very difficult to suture in place. While admittedly remote, there is also a bare possibility that the unit can work around and come offf as each stitch in turn moves through the gap between the ends.

It has now been found in accordance with the teaching of the instant invention that these and other shortcomings of the prior art anastomosis markers can, in large measure, be overcome by the simple, yet unobvious, expedient of providing a split ring of radiopaque material with loops at both ends and a third intermediate the ends that define eyes through which sutures can be passed permanently fastening same to the tissue at the exact site of the graft. The looped ends become blunted to a degree where they essentially eliminate any chance that they might scrape, puncture or otherwise damage the adjacent tissue. The split of course, enables the marker to be opened and passed around the vein after both ends thereof have been grafted onto the aorta. Depending upon the relative size of the ring and the vein it encircles, the loops at the ends can be left in spaced relation alongside one another where they must be sutured separately or overlapped in registered relation where the same suture or sutures will pass through both eyelets thus formed. The third eye formed intermediate the ends cooperates with the endloops to insure the fact that the marker remains precisely at the site of the anastomosis. Without the third eye, there is nothing to prevent the marker from tilting and providing the viewer with a false indication of the position of the graft much as is the case with the prior art tags fastened alongside thereof.

It is, therefore, the principal object of the present invention to provide a novel and improved radiopaque anastomosis marker.

A second object of the invention is to provide a device of the character described which is devoid of sharp ends and projections that might injure the adjacent tissue.

Another object of the invention herein disclosed and claimed is to provide a marker which locates the exact site of the anastomosis and is readily visible to the viewer fluoroscopically.

Still another objective of the within described invention is the provision of a marker for saphenous vein-aortic anastomoses and the like that includes eyelets susceptible of two or three point attachment on opposite sides of the graft to permanently fasten same in fixed position relative thereto.

An additional object is to provide an appliance of the type aforementioned which can be expanded or contracted as required to properly fit the anastomosis it is to encircle and locate.

Further objects are to provide a radiopaque anastomosis marker that is inexpensive, easy to implant, safe, versatile, trouble free, lightweight, compact and even decorative in appearance.

Other objects will be in part apparent and in part pointed out specifically hereinafter in connection with the description of the drawings that follows, and in which:

FIG. 1 is a perspective view showing the marker from a vantage point above and in front thereof;

FIG. 2 is an elevation showing in broken lines the spread position thereof as well as a fully closed position in which the end loops lie in overlapped relation;

FIG. 3 is an edge view; and,

FIG. 4 is a fragmentary perspective view illustrating how the marker is spread to pass around the vein and then sutured to the aorta in encircling relation to the anastomosis.

Referring next to the drawings for a detailed description of the present invention, the marker forming the subject matter hereof has been broadly designated by reference numeral 10 and it will be seen to take the general form of a split ring 12 sized to loosely encircle the site of an anastomosis 14 as shown in FIG. 4. Terminal eyelets 16 and 18 are provided at the free ends 20 of the ring while a medial eyelet 22 is located therebetween. The size of these eyelets is such as to easily pass the suture material 25 as well as the needle (not shown) by means of which they are permanently fastened in fixed position to the tissue 27 at the exact site of the anastomosis, again as shown in FIG. 4.

Next, directing the attention specifically to FIGS. 1, 2 and 3, the marker will be seen to comprise a length of springable or at least bendable, metal wire or, alternatively, ribbon fabricated from an inert material such as stainless steel that can be accommodated internally and which has been bent to form closed loops 24 at both ends and a third loop 26 in the middle, these loops constituting the aforementioned eyelets 16, 18 and 22. In the preferred form shown, end loops 24 comprise only a single coil of the wire while the third loop consists of a pair of coils arranged one atop the other in stacked relationship. Since the legs 28 of the ring that extend between the terminal eyelets and the medial one must be spread apart to admit the vein 30 therebetween, the double coil loop 26 provides a better spring action than a single one for obvious reasons although it is equally obvious that a single coil loop would suffice. Likewise, spring wire or ribbon is not essential to operation of the marker so long as it is bendable to the extent that the vein can be passed between its legs preparatory to reclosing them to produce the desired encircling relationship. The ring must not fit so tightly as to constrict the flow through the vein or artery it encircles, yet, at the same time it should fit closely enough to precisely identify the location of the anastomosis when viewed fluroscopically. In the particular application illustrated in FIG. 4, the sutures fasten the ring to the heart tissue directly despite the fact that the marker encircles the saphenous vein where a splice is made, the marker will, of necessity, have to be sutured directly to the tube it encircles.

Ordinarily, the three eyelets will be connected separetly to the adjacent tissue using so-called "interrupted" sutures although, depending upon the relative dimensions of the marker and vein it encircles, the legs can, if desired, be brought together until the terminal eyelets overlap one another in registered relation, whereupon, the suture of sutures used to fasten the marker in place can pass through both at once. Such an overlapped or stacked condition has been represented by broken lines in FIG. 2. There is no particular advantage achieved by stacking the terminal eyelets other than, perhaps, to produce an uninterrupted radiopaque band around the anastomosis. A narrow gap 32 left between the terminal ends is of little consequence insofar as locating the exact site of the graft and, under all but the most unusual circumstances, this is all that will exist therebetween.

Of prime importance in the construction of the marker is the elimination of any sharp or pointed surfaces that could conceivably scrape, puncture, or otherwise damage the adjacent tissue. The terminal loops at both free ends 20 adequately blunt the latter, especially when these ends terminate as shown in FIG. 2 in abutting relation to the leg in which they are formed to produce an essentially planar loop as opposed to a coiled one like the medial loop. A coiled loop on the end would, of necessity, leave the free end 20 exposed to a significantly greater degree where the likelihood of its scraping or otherwise damaging the adjacent tissue becomes greater.

What is claimed is:

1. A radiopaque marker for internal implantation as a means for locating the site of an anastomosis during subsequent fluoroscopic examination, comprising a one-piece split ring of a radiopaque material and having a substantially circular configuration, said ring formed with a first loop intermediate the ends thereof providing a spring normally urging the ends toward one another and defining a suture receiving opening for suturing the ring to adjacent tissue, and the ends of the rings formed into closed, second and third loops, respectively, thus defining suture receiving openings and at the same time eliminating exposed sharp ends, said ring and loops being substantially coplanar and the ring being spreadable to enable placement of the ring over a sutured-in-place vein, the suture receiving openings being substantially diametrically opposite one another, thus preventing tilting of a sutured in place marker.

2. A radiopaque marker as in claim 1, wherein the first loop comprises a pair of contiguous, superposed coils.

3. A radiopaque marker as in claim 2, wherein the second and third loops each comprise a single coil defined by the respective terminal end portion of the ring bent outwardly and rearwardly upon itself with the free end disposed against the adjacent end portion of the ring, thereby eliminating sharp ends.

4. A radiopaque marker as in claim 3, wherein the marker comprises stainless steel.

* * * * *